United States Patent
Amplatz et al.

(10) Patent No.: US 8,778,008 B2
(45) Date of Patent: *Jul. 15, 2014

(54) INTRAVASCULAR DELIVERABLE STENT FOR REINFORCEMENT OF VASCULAR ABNORMALITIES

(75) Inventors: Kurt Amplatz, St. Paul, MN (US); John C. Oslund, Blaine, MN (US); Patrick Russo, Vadnais Heights, MN (US); Xiaoping Gu, Plymouth, MN (US)

(73) Assignee: AGA Medical Corporation, Plymouth, MN (US)

( * ) Notice: Subject to any disclaimer, the term of this patent is extended or adjusted under 35 U.S.C. 154(b) by 1056 days.

This patent is subject to a terminal disclaimer.

(21) Appl. No.: 11/654,288

(22) Filed: Jan. 17, 2007

(65) Prior Publication Data
US 2007/0168019 A1 Jul. 19, 2007

Related U.S. Application Data

(63) Continuation-in-part of application No. 11/331,640, filed on Jan. 13, 2006.

(51) Int. Cl.
*A61F 2/06* (2013.01)
*A61F 2/82* (2013.01)
*A61F 2/852* (2013.01)

(52) U.S. Cl.
CPC .. *A61F 2/82* (2013.01); *A61F 2/852* (2013.01)
USPC ........................................ 623/1.13; 623/1.44

(58) Field of Classification Search
CPC ............. A61F 2/82; A61F 2/89; A61F 2/856; A61F 2/07; A61F 2/852; A61F 2002/075; A61F 2/072; A61F 2/077; A61F 2/061
USPC ........... 623/1.11, 1.13, 1.15, 1.16, 1.18, 1.32, 623/1.33, 1.34, 1.44, 1.5, 1.51, 1.53
See application file for complete search history.

(56) References Cited

U.S. PATENT DOCUMENTS

| 4,655,771 A | 4/1987 | Wallsten |
| 4,954,126 A | 9/1990 | Wallsten |

(Continued)

FOREIGN PATENT DOCUMENTS

| EP | 1477134 | 11/2004 |
| EP | 1645246 | 4/2006 |
| WO | WO 02/055125 | 7/2002 |

*Primary Examiner* — Dianne Dornbusch
(74) *Attorney, Agent, or Firm* — Armstrong Teasdale LLP

(57) ABSTRACT

A catheter deliverable stent/graft especially designed to be used in a minimally invasive surgical procedure for treating a variety of vascular conditions such as aneurysms, stenotic lesions and saphenous vein grafts, comprises an innermost tubular structure and at least one further tubular member in coaxial arrangement. In one embodiment, the innermost tubular structure is of a length ($L_1$) and is formed by braiding a relatively few strands of highly elastic metallic alloy. The pick and pitch of the braid are such as to provide relative large fenestrations in the tubular wall that permit blood flow through the wall and provide the primary radial support structure. A portion of the innermost tubular structure of a length $L_1$ is surrounded by a further braided tubular structure having relatively many strands that substantially inhibit blood flow through the fenestrations of the innermost tubular structure. The composite structure can be stretched to reduce the outer diameter of the stent/graft, allowing it to be drawn into a lumen of a delivery catheter. The catheter can then be advanced through the vascular system to the site of treatment and then released, allowing it to self-expand against the vessel wall. Various optional embodiments are disclosed that allow one skilled in the art to tailor the design to the specific application.

26 Claims, 3 Drawing Sheets

(56) References Cited

U.S. PATENT DOCUMENTS

| | | |
|---|---|---|
| 5,061,275 A | 10/1991 | Wallsten et al. |
| 5,064,435 A | 11/1991 | Porter |
| 5,366,504 A | 11/1994 | Andersen et al. |
| 5,383,925 A | 1/1995 | Schmitt |
| 5,476,508 A | 12/1995 | Amstrup |
| 5,741,325 A | 4/1998 | Chaikof et al. |
| 5,800,508 A | 9/1998 | Goicoechea et al. |
| 5,906,641 A | 5/1999 | Thompson et al. |
| 5,916,264 A | 6/1999 | Von Oepen et al. |
| 6,110,198 A | 8/2000 | Fogarty et al. |
| 6,129,756 A | 10/2000 | Kugler et al. |
| 6,152,956 A | 11/2000 | Pierce |
| 6,156,064 A | 12/2000 | Chouinard |
| 6,312,458 B1 * | 11/2001 | Golds .......................... 623/1.13 |
| 6,342,068 B1 | 1/2002 | Thompson |
| 6,344,052 B1 | 2/2002 | Greenan et al. |
| 6,488,705 B2 | 12/2002 | Schmitt et al. |
| 6,585,758 B1 | 7/2003 | Chouinard et al. |
| 6,669,720 B1 | 12/2003 | Pierce |
| 6,695,875 B2 | 2/2004 | Stelter et al. |
| 6,709,451 B1 | 3/2004 | Noble et al. |
| 6,709,455 B1 | 3/2004 | Chouinard |
| 6,860,900 B2 | 3/2005 | Clerc et al. |
| 6,932,837 B2 | 8/2005 | Amplatz et al. |
| 7,108,716 B2 | 9/2006 | Burnside et al. |
| 2001/0049554 A1 * | 12/2001 | Ruiz et al. .................... 623/1.35 |
| 2002/0052643 A1 | 5/2002 | Wholey et al. |
| 2002/0052645 A1 | 5/2002 | Kugler et al. |
| 2003/0023299 A1 * | 1/2003 | Amplatz et al. ............. 623/1.13 |
| 2003/0130724 A1 | 7/2003 | DePalma et al. |
| 2003/0149473 A1 | 8/2003 | Chouinard et al. |
| 2004/0010308 A1 * | 1/2004 | Zafrir-Pachter et al. ...... 623/1.35 |
| 2004/0044396 A1 * | 3/2004 | Clerc et al. .................. 623/1.13 |
| 2004/0059406 A1 | 3/2004 | Cully et al. |
| 2004/0098095 A1 * | 5/2004 | Burnside et al. ............. 623/1.13 |
| 2004/0162606 A1 | 8/2004 | Thompson |
| 2004/0193245 A1 | 9/2004 | Deem et al. |
| 2005/0033405 A1 | 2/2005 | Solovay |
| 2005/0267568 A1 | 12/2005 | Berez et al. |

* cited by examiner ions, and saphenous vein grafts by reinforcing, excluding, bridging, or lining a blood vessel. Although emphasis is given to such a stent or graft specifically designed for addressing aneurysms and particularly iliac artery and abdominal aortic aneurysm (AAA), other embodiments suitable for saphenous vein graft (SVG), dialysis graft, and carotid arteries are also disclosed.

INTRAVASCULAR DELIVERABLE STENT FOR REINFORCEMENT OF VASCULAR ABNORMALITIES

CROSS-REFERENCE TO RELATED APPLICATION

The present application is a continuation-in-part of application Ser. No. 11/331,640, filed on Jan. 13, 2006, the entirety of which is incorporated herein by reference for any purpose.

BACKGROUND OF THE INVENTION

I. Field of the Invention

This invention relates generally to an intravascular deliverable stent or graft. In particular this invention relates to a unique stent or graft for the treatment of aneurysms, lesions, and saphenous vein grafts by reinforcing, excluding, bridging, or lining a blood vessel. Although emphasis is given to such a stent or graft specifically designed for addressing aneurysms and particularly iliac artery and abdominal aortic aneurysm (AAA), other embodiments suitable for saphenous vein graft (SVG), dialysis graft, and carotid arteries are also disclosed.

II. Discussion of the Prior Art

An aortic aneurysm is a weak area in the aorta, the main blood vessel that carries blood from the heart to the rest of the body. The aorta extends upwards from the heart in the chest and then arches downwards, traveling through the chest (the thoracic aorta) and into the abdomen (the abdominal aorta). The normal diameter of the abdominal aorta is about one inch (25 mm). As blood flows through the aorta, the weak area bulges like a balloon and can burst if the balloon gets too big.

Most commonly, aortic aneurysms occur in the portion of the vessel below the renal artery origins. The aneurysm may extend into the vessel's supplying the hips and pelvis, including the iliac arteries.

Once an aneurysm reaches 5 cm (about 2 in.) in diameter, it is usually considered necessary to treat to prevent rupture. Below 5 cm, the risk of the aneurysm rupturing is lower than the risk of conventional surgery in patients with normal surgical risks. The goal of therapy for aneurysms is to prevent them from rupturing. Once an AAA has ruptured, the chances of survival are low, with 80-90 percent of all ruptured aneurysms resulting in death. These deaths can be avoided if the aneurysm is detected and treated before it ruptures and ideally treated at an early stage (smaller aneurysm) with a lower risk procedure.

Most aortic aneurysms occur in the abdominal aorta, the main cause being arteriosclerosis. This is a condition in which fatty deposits are laid down in the walls of the arteries, which are less elastic and weaker as a result. Major risk factors for arteriosclerosis are smoking and high blood pressure as well as genetic factors.

AAA can be diagnosed from their symptoms when they occur, but this is often too late. They are usually found on routine physical examination and chest and abdominal X-rays. On examination, a doctor may feel a pulsating mass in the abdomen. If the doctor suspects an aneurysm, he/she will probably request that an ultrasound scan be carried out. Other scans, such as computerized tomography (CT) and magnetic resonance imaging (MRI) may also be performed. These scanning techniques are very useful for determining the exact position of the aneurysm.

The surgical procedure for treating AAA involves replacing the affected portion of the aorta with a synthetic graft, usually comprising a tube made out of an elastic material with properties very similar to that of a normal, healthy aorta. This major operation is usually quite successful with a mortality of between 2 and 5 percent. Even during surgery, the risk of death from a ruptured AAA is about 50%.

More recently, instead of performing open surgery in undertaking aneurysm repair, vascular surgeons have installed an endovascular stent/graft delivered to the site of the aneurysm using elongated catheters that are threaded through the patient's blood vessels. Typically, the surgeon will make a small incision in the patient's groin area and then insert a delivery catheter containing a collapsed, self-expanding or balloon-expandable stent/graft to a location bridging the aneurysm, at which point the stent/graft is delivered out from the distal end of the delivery catheter and allowed or made to expand to approximately the normal diameter of the aorta at that location. The stent/graft, of course, is a tubular structure allowing blood flow through the lumen thereof and removing pressure from the aneurysm. Over time, the stent/graft becomes endothelialized and the space between the outer wall of the stent and the aneurysm ultimate fills with clotted blood. At this time, the aneurysm is no longer subjected to aortic pressures and thus will not continue to grow.

In treating AAA, it is important that the stent or graft be accurately placed so as not to occlude blood flow through the renal arteries which branch off from the abdominal aorta.

In the Amplatz et al. U.S. Pat. No. 6,932,837, there is described a collapsible stent/graft designed for grafting a lumen of a selected blood vessel or other tubular organ. The stent/graft comprises a woven or braided fabric made from a plurality of strands of a shape memory alloy. The fabric is formed as a tube and each end of the device is open to allow fluid flow therethrough. The device can be longitudinally stretched to thereby reduce its diameter, allowing it to be inserted within the lumen of a delivery catheter. When ejected from the distal end of the delivery catheter, the stent/graft will self-expand to a predetermined outer diameter sufficient to engage the wall of the tubular vessel being treated.

While the device in the '837 patent is altogether suitable for use as a coronary stent, it is not well suited for the intravascular treatment of AAA. That device is of a uniform weave, but necessarily is of a wire density that is insufficient to limit the exposure of the aneurysm to aortic blood pressure. Should this stent/graft also encroach upon the ostia of the renal arteries, it could restrict blood flow to the kidneys.

A need, therefore, exists for a stent/graft that can be placed using an endovascular approach in the treatment of AAA, but that will not unduly occlude blood flow to the kidneys. The present invention provides such a device.

Aneurysms may also occur in the thoracic aorta where the renal arteries are not involved in the procedure, or in other arteries in the body. Depending on where the aneurysm is in relation to other branch vessels, different design variations may be needed. In some cases, where no branch vessels are involved, the stent/graft wall may be uniform throughout. In cases involving the upper aorta, one portion of the stent/graft, either the proximal, distal or area in between, may need to have a portion of the stent/graft wall with larger openings to allow adequate flow to the carotid arteries as compared to the balance of the stent/graft where the wall may have much smaller openings.

Regardless of the aneurysm site being treated, there is a need for an improved stent or vascular graft that can be collapsed to a very small deliverable diameter to reduce the arterial puncture access sheath size, trauma to the vessel at the access site and to provide for a smaller, more trackable delivery system that is less traumatic to the vasculature. There is also a need for a low profile stent or graft that provides vascular support, exclusion of aneurysms, and a surface for rapid endothelialization. The invention herein provides such benefits.

In the field of interventional cardiology, it is now becoming routine to treat stenotic lesions, in the vascular system, including saphenous vein grafts and carotid arteries, using balloon angioplasty to render more patent a partially occluded blood vessel and to attempt to thwart restenosis by placement of a stent at the site of the treated lesion.

Stents used in these procedures must be capable of assuming a reduced diameter configuration for delivery through a guide catheter or arterial sheath, but which is either self-expanding upon exit of the distal end of the guide catheter or "balloon expandable".

In carrying out a balloon angioplasty procedure with stenting, the Seldinger technique is frequently used to gain access to the vascular system and a tubular introducer having a hemostatic valve for preventing blood loss is inserted through the puncture wound from the skin into the artery. In order to perform the procedure via percutaneous access without surgical cut down to expose the femoral artery, an introducer sheath smaller than 14 Fr (typically 6-8 Fr) is required in most patients. The smaller the introducer sheath, the less trauma to the tissue and the easier it is to place and to close the arterial puncture after the procedure. In some cases a long arterial sheath substitutes for a short vascular access sheath and provides a guiding path for delivery of devices to a site proximal the target treatment location. In other cases, a guide catheter is inserted through the introducer sheath and routed through the vascular system until the distal end portion of the guide catheter is disposed at the ostium of a selected artery having the stenotic lesion. Recently, steerable sheaths have been available for difficult to reach locations where sharp bends are encountered.

Next, a catheter may be advanced over a guide wire through the sheath or guide catheter, through the artery to the target treatment site. The catheter may be a balloon catheter, with or without a balloon expandable stent mounted over the balloon, or may be a delivery catheter for a self expanding stent. Treatment typically involves dilation of the stenotic lesion, followed by placement of a stent at the lesion site. Upon inflation of the balloon, the stenotic region of the artery having a restriction to flow is expanded in diameter to restore normal blood flow through the arterial segment. A balloon expandable or self expanding stent may next be placed in the dilated lesion site to maintain the vessel wall in the expanded diameter state. Balloon expandable stents are placed by inflating a balloon having a stent mounted thereon at the lesion site. Self expanding stents are typically placed by pulling back a sheath covering a compressed stent mounted at the distal end of the catheter. Following self expansion of the stent a balloon dilatation may optionally be used to seat the stent and ensure full expansion. Following the treatment, the catheter, guide wire, sheath, etc. are removed from the body and the vascular access site sealed by compression or other sealing means available.

Stents intended for use in percutaneous transluminal angioplasty applications come in various lengths and diameters to generally approximate the lesion length and normal range of vessel inside diameters at the various treatment sites throughout the body.

Saphenous vein graft (SVG) treatment, following a previous coronary by-pass procedure, often occurs after aging grafts become diseased and filled with a soft grumous material that can easily embolize during stenting or angioplasty. Such emboli can cause obstructions in the coronary arteries downstream to which the grafts are connected.

There is a need for a stent or graft that can be delivered in a very low profile in the collapsed state and that can line the SVG, providing vessel support, as well as preventing emboli from the SVG wall from reaching the coronary arteries.

Another recent treatment of lesions involves the carotid arteries and, in particular, treating the lesions with self expanding stents following balloon angioplasty. Since these arteries, internal carotids, lead to the brain and such lesions often contain friable plaque that can break off and cause strokes, it is necessary to deploy a distal filter or other proximal occlusion/extraction means, during the procedure to prevent emboli from reaching the brain during the procedure. Although this protection means helps to prevent emboli during the procedure, the stent itself does not provide adequate protection for preventing emboli after the stent deployment procedure due to the large open areas in the stent at the vascular wall surface.

There is a need for a stent for the carotid arteries that provides adequate vascular support as well as provides protection from emboli, and therefore stroke prevention, after the procedure is completed and the procedural protection systems are no longer in place.

In attempts to anchor prior art stents against unwanted migration following implant, vessel wall-engageable hooks are believed to cause damage to the endothelium and the situs of stenotic lesions. Thus, a need also exists for a stent or grant that is self-anchoring without requiring tissue penetrating hooks.

SUMMARY OF THE INVENTION

The present invention provides a catheter-deliverable, endovascular stent/graft for treating vascular abnormalities, such as AAA, aneurysms in the thoracic aorta or other locations, SVGs and lesions, particularly in the carotid arteries that comprises an innermost tubular structure having a first length surrounded by at least one further tubular structure with a second length and means for connecting the structures together and whereby at least one of the innermost or further tubular structure(s) provides substantially more "radial support" to the stent/graft than the other structure.

The innermost tubular structure comprises a plurality of braided wire strands exhibiting highly elastic characteristics, preferably a shape memory alloy. If the innermost structure is chosen as the primary radial support member of the stent/graft, the pick and pitch of the braid are chosen to define openings sufficiently large so as to not materially impede blood flow through the wall of the innermost tubular structure. The at least one further tubular structure also comprises a plurality of braided wire strands. If the further tubular structure(s) is not the primary radial support member of the stent/graft, the wire strands of the further braided tubular structure also comprise a shape memory alloy and the braid has a pick and pitch which define openings sufficiently small so as to substantially preclude blood flow therethrough.

The wire diameter of the primary radial support member is chosen to provide the primary radial support to the arterial wall to anchor the stent/graft while also being sufficient to exert radial force to the adjoining connected tubular structure (s) to urge the structures against each other and against the vessel wall.

The diameters of the wires of the non-primary support structure(s) are smaller and in greater quantity than the diameter and number of wires that comprise the radial support member. The radial expansion force is sufficient to self-expand the structure. Because the stent/graft of the present invention is designed to expand to a diameter greater than that of the vessel at the treatment site and because of the tiny fenestrations present, rapid endothelialization takes place. Thus, the need for anchoring hooks as in prior art stent/grants is obviated.

It is contemplated that the radial support structure of the stent may be the innermost tubular structure, a middle further tubular structure or an outermost further tubular structure, as desired, for a particular use. The radial support member has fewer, but larger diameter wires with braided openings which do not inhibit blood flow through the braid, compared to the non-radial support member which has small braid openings that do inhibit blood flow. In a self-expanding stent constructed in accordance with the teachings of the present invention, the radial force exerted by the radial support layer exceeds that of the occluding layer by about 80 to 90%.

Longitudinal stretching of the coaxially disposed innermost and further tubular structures reduces the outer diameter of the device sufficiently to permit it to be loaded into the lumen of a low profile endovascular stent/graft delivery catheter. The release of the stent from the delivery catheter allows its outer diameter to self-expand back to its original predetermined diameter as limited by the wall of the vessel.

In order to achieve the same length of all layers during device collapse for delivery and self-expansion, it is desirable to have the braid pitch of each tubular structure at approximately the same angle.

It is also desirable to have the braided layer ends progressively displaced toward the stent/graft center as one moves from the innermost tubular structure ends to the outer, further tubular structure ends. Assuming wire pitch in all layers is essentially the same, this makes the inner layer the longest, the middle layer a bit shorter and the outer layer the shortest in the construction of a three layer graft. This helps with eventual deployment in that it prevents the loose wire ends of the different layers from interacting and preventing another layer from fully deploying as the layers slide axially as they shorten or lengthen when moving between the collapsed and the expanded states. Alternatively, one may reverse the process making the outermost structure the longest with the innermost structure the shortest. In a particular configuration where the stent/graft has three structural braided members and whereby the middle structure is the primary radial support member, the innermost and outermost structural members may be shorter than the middle structural member.

In the preferred embodiment for treatment of AAA, the innermost tubular structure is the stent/graft primary radial support member and the distal end of the braid extends significantly distal to the distal end of the at least one further tubular structure. This distal portion of the innermost tubular structure can overlay the juncture of the patient's renal arteries within the abdominal aorta while the further tubular structure(s) surrounds the innermost tubular structure, extends proximal to the renal arteries and bridges the abdominal aortic aneurysm, but without the stent/graft blocking blood flow to the kidneys. It should be noted that a stent/graft could be configured whereby the proximal and distal sections are reversed for treating an aneurysm above or upstream of the renal arteries.

In another embodiment for aneurysm, where no significant branch arteries are present, or in applications such as SVGs, the length of the innermost layer and at least one further tubular structure are substantially the same length except for the end displacement of adjacent braided layer ends as previously explained.

It is generally preferred to have the radially stiffest layer as the innermost tubular structure for deployment for obtaining full apposition of all layers against the wall of the vessel in which the graft is being placed. However it is preferred to have the radially stiffest layer on the outside with the denser layers on the inside to get the optimum healing response and a smoother inside vessel wall surface for endothelial growth. There may well be a particular application where the primary radial member should be the middle structural member to provide for a smooth structural member on both inner and outer surfaces. The choice may depend on the specific application of the stent/graft.

In certain anatomical situations, it may be required to protect flow through side branch vessels while providing vascular support, exclusion of an aneurysm or protection from embolism by lining a segment of the vessel. In such situations it may be desirable to have a middle portion of the stent/graft with only the primary radial support tubular structure with larger opening between the wires to allow side branch flow without restriction. In this case, the stent/graft would have at least two further tubular structures displaced from the middle, more open portion, either as innermost structures or outermost structures or both. As described before, the wire ends of one structural tubular member would be offset from the end wires of an adjacent tubular structure to facilitate expansion and contraction of the stent/graft.

DESCRIPTION OF THE DRAWINGS

The foregoing features, objects and advantages of the invention will become apparent to those skilled in the art from the following detailed description of a preferred embodiment, especially when considered in conjunction with the accompanying drawing in which.

DESCRIPTION OF THE PREFERRED EMBODIMENTS

Figure 1:
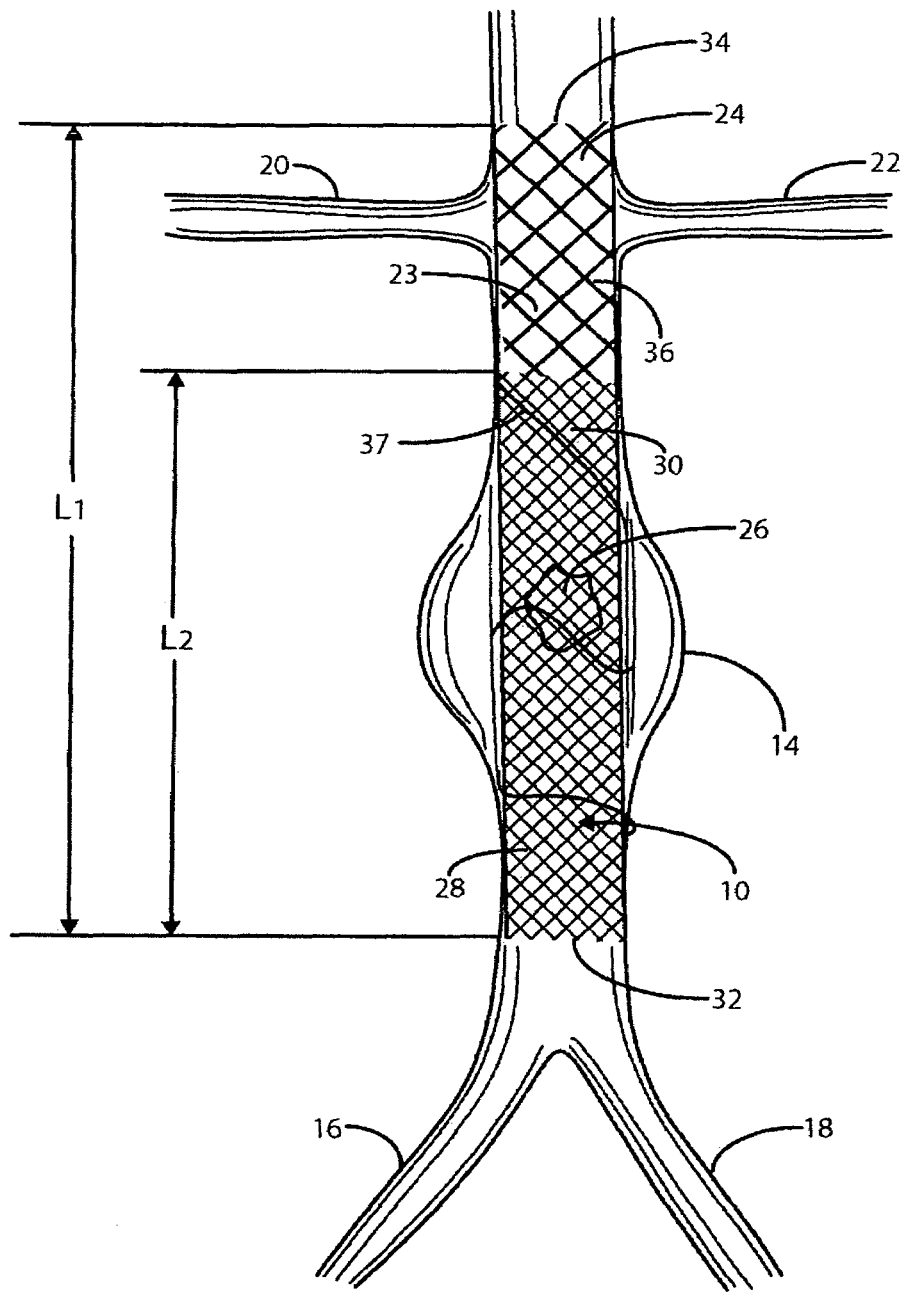
FIG. 1 is a side elevation view of the stent/graft of the present invention disposed in a patient's abdominal aorta so as to bridge an aneurysm, the abdominal aorta being shown in sectional view so as not to obscure the stent/graft.

Referring to FIG. 1, there is indicated generally by numeral 10 the preferred embodiment of the stent/graft constructed in accordance with the present invention. The stent/graft 10 is shown in place in a segment of the abdominal aorta 12 having an aneurysm 14. At its lower end, the abdominal aorta 12 branches into the left and right common iliac arteries 16 and 18. Also shown in FIG. 1 are renal arteries 20 and 22 leading to the kidneys (not shown).

The stent/graft 10 comprises an innermost tubular structure 23 of a first length ($L_1$) and at least one further tubular structure 26 of a length L2, both structures having a predetermined similar diameter. The stent/graft may have an overall length $L_1$ in the range of 12 to 16 cm, preferably 14 cm. and a length L2 in the range of 8 to 12 cm, preferably 10 cm.

The innermost tubular structure comprises a first plurality of braided wire strands 24, preferably of a shape memory alloy, such as Nitinol. The braid comprising the innermost tubular structure 23 has a predetermined pick and pitch to define openings through the structure that are sufficiently large so as not to materially impede blood flow through its fenestrated wall. The wire strands may have a diameter in a range of from 0.002 to 0.012 inch and tubular structure 23, is designed to provide an adequate radial outward force necessary for self-expansion/vascular support/anchoring of the stent/graft 10. This could also be the outer graft layer if the layers are tied together so that the expansion of the other layers follows suit with the expansion of the frame.

To achieve adequate vascular support for anchoring the stent/graft in the region of the renal arteries, the innermost tubular structure's self expanding diameter is sized to be larger than the native vessel diameter to exert a holding force against the native vessel. This oversizing of the stent/graft diameter may be in the range of 10-20%. This oversizing may, alternatively, be limited to the portion of the device involved in anchoring near the renal arteries. This may be beneficial since it is not desirable to put an outward radial force on the aneurismal section.

At least one further tubular structure 26, with a predetermined length portion ($L_2$) and a predetermined diameter, is placed in coaxial surrounding relationship of the innermost tubular structure where the further tubular structure 26 is of a shorter length than that of the innermost tubular structure 23.

The further tubular structure surrounding the innermost tubular structure is comprised of a second plurality of braided wire strands 28 that is significantly greater in number than the first plurality of braided wire strands making up the innermost tubular structure. The strands 28 are also of a shape memory alloy and they are braided so as to have a pick and pitch to define openings sufficiently small so as to substantially preclude blood flow through the wall thereof.

Without limitation, the innermost tubular structure 23 may comprise 36-144, (preferably 72) strands of wire ranging in diameter from 0.002 to 0.010 in. (preferably 0.006) woven so as to exhibit fenestrations with an area of about 0.001 to 0.002 sq. in., preferably 0.0015 sq. in. The further tubular structure 26 may then comprise 72-288, preferably 144 wires ranging in diameter from 0.001 to 0.005 in., preferably 0.0025 in., formed of a shape memory alloy, such as Nitinol, that are braided so as to define significantly smaller fenestrations having an area of from 0.00015 to 0.0003 sq. in., preferably 0.00025 sq. in., which are sufficiently small so as to substantially preclude blood flow through the portion of the stent/graft 10 of the length $L_2$. Inner and outer braided layers have pitch rates that are about equal to obtain desirable collapse and expansion characteristics, such as maintaining a uniform overall length. It should be noted that as used herein "substantially preclude or impede flow" shall mean, functionally, that blood flow may occur for a short time, preferably about 15-45 minutes, but that the body's clotting mechanism or protein or other body deposits on the braided wires results in occlusion or flow stoppage after this initial time period. This may be clinically represented by no contrast flow through the stent/graft wall after the 15-45 minute period as viewed by fluoroscopy after a contrast injection.

In accordance with the present invention, even smaller fenestrations can be provided over the length $L_2$ by having a second, outermost, tubular braided structure 30 coaxially surrounding the intermediate tubular structure 26 that surrounds the innermost tubular structure 23. This second and outermost tubular structure 30 would also extend the length $L_2$ (slightly shorter due to wire end offset) and may be identical in its braided configuration to the further tubular structure 26, e.g., 72-288, preferably 144 strands of 0.001 to 0.005 diameter Nitinol wire braided so as to have effectively 0.0001 (0.010 in.×0.010 in.) sq. in. openings.

The stent/graft tubular structural layers are "stitched" together in the center of the structure using platinum radiopaque stranded wire, diameter range of 0.002 to 0.006, preferably 0.003 in., at 3-5 locations around the circumference. This has two benefits—it allows the implanting medical professional to know where the center of the graft is for centering the stent/graft in the center of the aneurysm and it also allows the multiple braided layers to more freely move during collapse and expansion. By holding the layers together in the center, the relative position of the layers in relation to one another are fixed, however, the ends of the layers can float somewhat freely in relation to one another to allow for full radial deployment without much interaction with one another. If braid pitches between layers are not identical, stitching the graft in more than one location along the length leads to bunching which leads to high profiles and undesirable interaction between the braided layers. Platinum wire or ribbon stitching may also be placed at locations other than the center of the stent/graft, if the braided tubular structures have substantially the same pitch angle. Other types of connectors, such as radiopaque rivets may be used as an alternative to platinum wire/ribbon. Not all connectors need to be radiopaque.

It is also contemplated that one or more radial (helical) stitches, as at 37 in FIG. 1, may be used to hold all braided layers tightly together along the entire length of the graft (rather than just in the center) to prevent any separation of the layers once the device is implanted. The radial stitches could be Nitinol and could be heat set at the same time the graft is heat set. These helical stitches could be sewn into the braid at approximately the same pitch as the braided layers. One could stitch to follow every $3^{rd}$ or $5^{th}$ wire, for example, and weave in and out of the braid in a helical pattern until the entire length of the braid was sewn. The inner structure wires would likely be followed with this stitching.

It is contemplated that the stent/graft 10 be fabricated using the method set out in U.S. Pat. No. 6,123,715 to Curtis Amplatz, the teachings of which are hereby incorporated by reference. The innermost structure 23 could be braided to form a tubular fabric as would the further tubular structure or structures 26. The outer braided tube or tubes would then be concentrically disposed over the innermost tubular structure and the combination would be placed about a cylindrical mandrel of the desired outer diameter for the stent/graft. This assembly would then be heated to a predetermined temperature and for a length of time sufficient to heat set the tubular structures to the diameter of the mandrel. The opposite free ends 32, 34 of the strands comprising the innermost tubular structure 23 may be flared radially outward by 10° to 30° to provide improved apposition with the inner wall of the aorta.

Following removal from the mold, the two or more coaxial braided tubes may be held together by one or more connecting members, e.g., a few radiopaque platinum wires or, alternatively, suture stitches. Such stitches are preferably placed at approximately the mid-point of the length of the tubular structure to facilitate fluoroscopic placement and so that the stent/graft can be elongated both in the proximal and distal direction for insertion into a delivery system. As such, the suture stitches successfully hold the coaxially braided tubes together yet permit portions of the individual coaxial braided tubes to move relative to each other as the stent is stretched for insertion into the delivery system and as it self-expands to engage the aortic wall and budge the aneurysm.

It is also contemplated that the thus-formed stent/graft can be coated with a drug-eluting polymer for reducing embolization or displacement of grumous material. The drug-eluting polymer may be selectively coated on the open weave or closed weave segments.

In use, the thus-formed stent would be releasably affixed at its proximal end to a pusher catheter in the manner described in the copending Amplatz patent application Ser. No. 11/121,386, filed May 4, 2005 and entitled "System for the Controlled Delivery of Stents and Grafts". The stent would then be drawn into a lumen of an intravascular delivery catheter. The delivery catheter would be introduced into the patient using the well-known Seldinger technique and then threaded through the vascular system until a distal end of the delivery catheter is proximate an aneurysm to be treated. With the stent and the pusher catheter held stationary, the delivery catheter is drawn in the proximal direction to eject the stent from the distal end of the delivery catheter where the stent then self-expands to engage the aortic wall with the portion of length $L_2$ in FIG. 1 bridging the aneurysm being treated. The portion of the innermost tubular structure that extends beyond the distal end of the further tubular structure may overlay the ostia of the renal arteries 20 and 22. However, because of the open weave construction of that portion of the inner tubular structure, it does not significantly impede blood flow through the renal arteries or create a stenosis. The added length of the stent/graft 10 provided by the extension of the innermost tubular structure 23 beyond the distal end of the further layer(s) 26, 30 serves to better stabilize the stent/graft within the abdominal aorta, preventing its displacement before endothelialization can occur.

Figure 2:
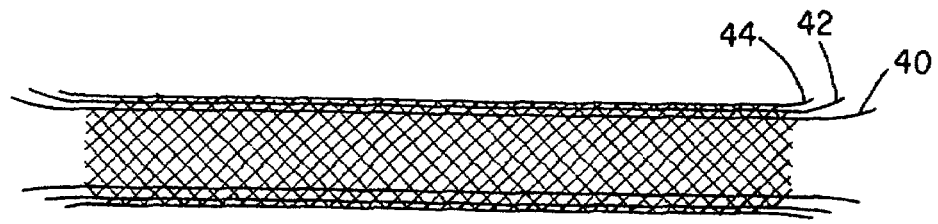
FIG. 2 is a stent/graft view of a second embodiment where the tubular structures are roughly the same length with the wire ends offset.
Figure 3:
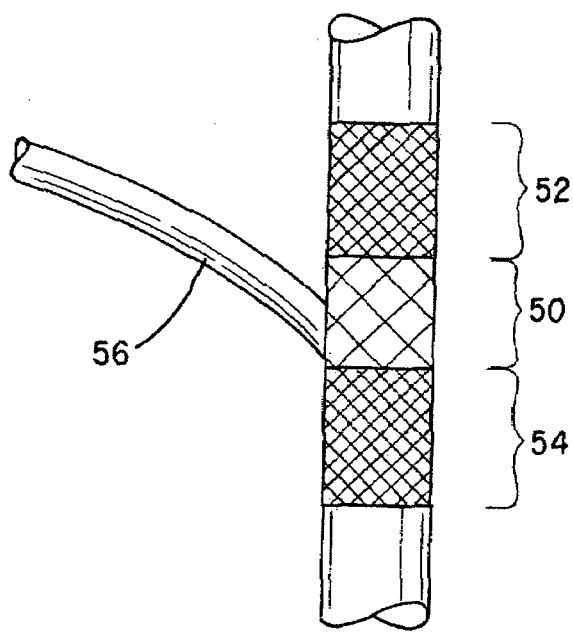
FIG. 3 is a stent/graft view of a third embodiment where the stent/graft has a middle portion more open to flow than the end portions.
Figure 4:
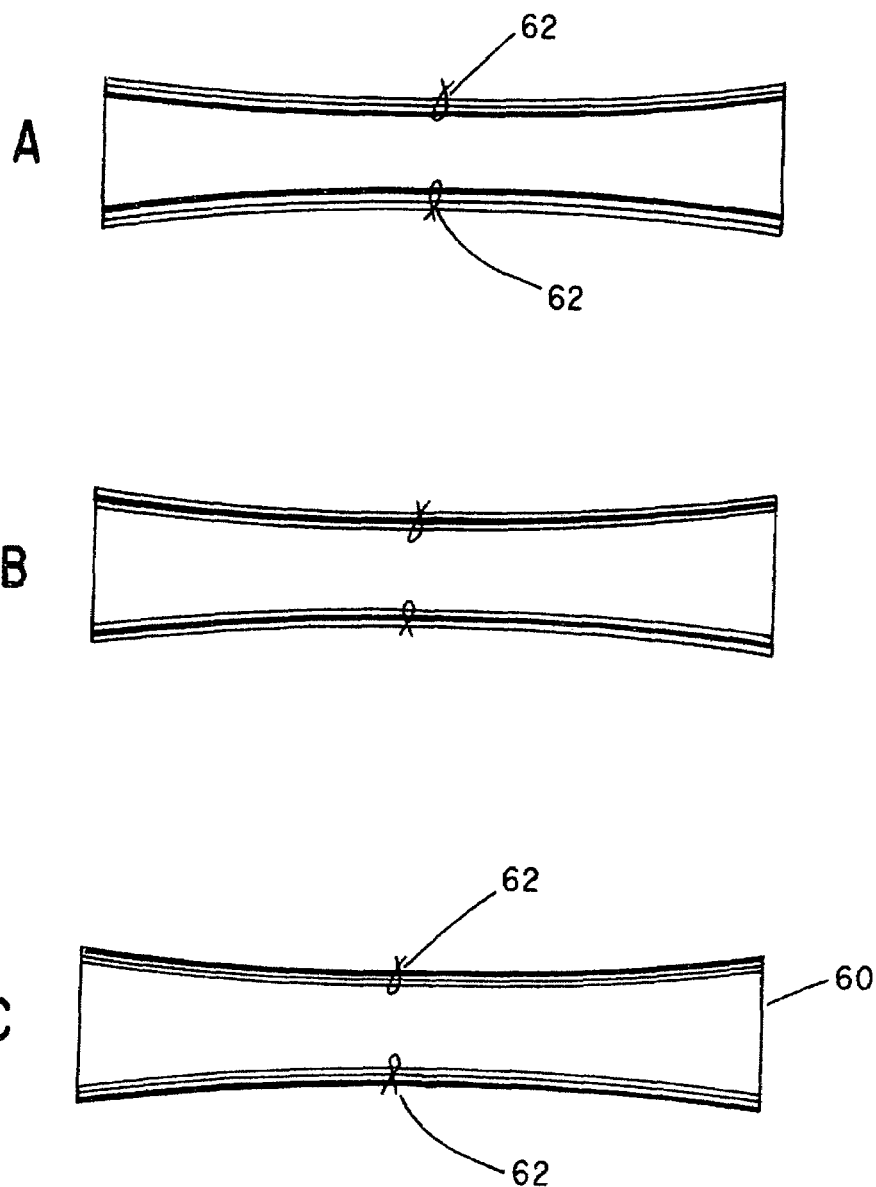
FIGS. 4 A, B, C show the various embodiments where the primary radial structure member is the innermost, middle, or outermost structural member, respectively.

Alternative embodiments are shown in FIGS. 2, 3, & 4 A,B,C. In all of the alternative embodiments, the individual parameters regarding number of wires, wire diameter, pitch, and fenestration size for either a primary radial support tubular member or a non-primary radial support tubular member are similar to, but not limited to, those parameters as described in the AAA stent/graft preferred embodiment, FIG. 1.

In FIG. 2 the innermost tubular structure 40 and at least one further tubular structure 42 and 44 are shown as having substantially the same length, with the exception of the wire end offset of adjacent structures, whereby the wire ends are offset toward the center of the stent/graft. The offset may range from 0.020 to 0.100 in., and preferably is about 0.050 in.

In another embodiment of the stent/graft shown in FIG. 3, the stent/graft has a middle portion 50 more open to flow than the end portions 52 and 54. The middle portion 50 in this preferred embodiment represents the primary radial support layer only, with at least one further tubular structure on both ends from the middle more open fenestration portion. This particular embodiment may be suited, for example, to a carotid lesion application, where the stent/graft is positioned across the carotid bifurcation in such a manner that the middle, more open fenestration portion allows relatively unrestricted blood flow from the common carotid through the wall of the stent/graft into the external carotid artery 56 while axial flow proceeds to the internal carotid artery.

FIGS. 4A, B and C show alternative embodiments where the primary radial support structure, represented as a heavy line, varies in its placement between the innermost structural layer (FIG. 4A); middle structural layer (FIG. 4B) and outermost structural layer (FIG. 4C). These construction alternatives could be applied to any of the embodiments shown in FIG. 1, 2 or 3.

Each embodiment may be alternatively constructed by using materials having elastic properties other than Nitinol, such as spring stainless steel, Elgiloy, or hastalloy or a mixture of metal and plastic fibers. The metal and plastic fibers may be combined in the same layer; alternatively the device may be constructed in such a manner that each layer is made from a different material. Depending on the individual material selected, the wire diameter, number of wires and pitch may be altered to achieve the desired properties of the stent/graft. In any of the embodiments, as in that of FIG. 2, the individual tubular members may optionally have the end wires heat set radially outward 10-30 degrees from the longitudinal axis of the stent/graft, to improve end wire seating and anchoring in the vessel. This also makes it less likely that passage of subsequent catheters through the stent/graft will hang up on the wire ends.

Another embodiment contemplated is a stent/graft where there are two further braided tubular structures which are not primary radial support structures with the variation being that the two further structures are formed from one tubular member partially averted to create two layers. FIG. 4C shows an embodiment where the innermost two layers are formed from a single tubular braid of a length 21 that is averted to form a structure of a length L. Heat setting the folded end facilitates this structure.

A further embodiment of the stent/graft pertains to all of the previous embodiments but is differentiated by the manner in which the stent/graft is delivered. In all the previous embodiments the stent graft is a unified device made of attached tubular, concentric structures that are all delivered together by a single delivery catheter in a single step. In this further embodiment, the individual tubular structures are delivered one at a time in-vivo in separate procedural steps starting with the outermost tubular structure and next delivering the adjacent structure inside the previous structure. In this case the structures are not bonded together by stitching as at 62 in FIG. 4, but each individual structure may have radiopaque markers by stitching to facilitate placing the structure relative to the treatment site. The markers may be positioned such that the operator places the markers from various structures so they lie in the same plane transverse to the vessel. The stent/graft created in-vivo by serial delivery of individual structures is the same as all previous embodiments with the exception that the multiple structures are not stitched together, but are locked in place by the radial pressure of the innermost layer which would preferably also be the primary radial support layer.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

The invention claimed is:

1. A preassembled catheter deliverable stent/graft for treating a vascular abnormality in a vessel wall, comprising:
   an innermost tubular structure surrounded by at least one outer tubular structure; and
   at least one connecting member joining, prior to stent/graft delivery, said innermost tubular structure and outer tubular structure to form the preassembled catheter deliverable stent/graft,
   said innermost tubular structure and said outer tubular structure comprising braided wires of a highly elastic metallic alloy;

at least one of said innermost tubular structure and said outer tubular structure exhibits fenestrations whose open area is less than 0.002 square inches, wherein the braided wires are configured to be stretched longitudinally to reduce radial dimension thereof for facilitating insertion of the stent/graft into a catheter and upon extraction from the catheter at the site of treatment, the stent/graft self expands to engage the vessel wall.

2. The catheter deliverable stent/graft of claim 1 wherein one of the tubular has a length $L_1$ and comprises a primary radial support structure which permits relatively unrestricted blood flow through the wall of said one tubular structure and where another of the tubular structures has a length $L_2$ and inhibits blood flow through the wall of the tubular structure.

3. The catheter deliverable stent/graft of claim 2 where the Length $L_1$ is greater than the length $L_2$.

4. The stent/graft of claim 3 where the tubular structure of length $L_2$ is disposed at one end of the tubular structure of length $L_1$.

5. The stent/graft of claim 2 wherein the primary radial support structure is sized in relation to a vessel wall at a target site to provide anchoring of said stent/graft.

6. The stent/graft of claim 5 wherein the primary radial support structure has a diameter when unconstrained that is in a range of from 10% to 20% greater than the vessel wall's diameter at the target size.

7. The stent/graft of claim 2 where $L_1$ and $L_2$ are substantially the same.

8. The stent/graft of claim 2 wherein said at least one connecting member is positioned generally midway along the length $L_2$.

9. The stent/graft as in claim 8 wherein said at least connecting member comprises a suture stitch.

10. The stent/graft as in claim 9 wherein the suture stitch is of a radiopaque material.

11. The stent/graft of claim 2 wherein the innermost tubular structure comprises said primary radial support structure.

12. The stent/graft of claim 2 wherein the one tubular structure of the length $L_1$ is in surrounding coaxial relation with respect to said another tubular structure of length $L_2$.

13. The stent/graft as in claim 2 wherein a thrombogenesis modifying coating is selectively applied to the structures having a length $L_1$ and a length $L_2$.

14. The stent/graft as in claim 2 wherein the structure of length $L_1$ exhibits fenestrations whose open areas are about 0.001 to 0.002 square inches and wherein the structures of length $L_2$ exhibit fenestrations whose open areas are about 0.0001 to 0.0003 square inches.

15. The stent/graft as in claim 2 wherein a radial expansion force exhibited by the structure of length $L_1$ exceeds that of length $L_2$ by about 80 to 90%.

16. The stent/graft as in claim 1 wherein the innermost tubular structure is surrounded by two outer tubular structures that are axially spaced relative to one another by a predetermined distance.

17. The stent/graft of claim 1 wherein the highly elastic metal alloy is a shape memory alloy.

18. The stent/graft of claim 17 wherein the shape memory alloy is Nitinol.

19. The stent/graft as in claim 1 wherein said at least one connecting member comprises a continuous helical stitching pattern along a length dimension of the stent/graft.

20. The stent/graft as in claim 1 wherein the innermost tubular structure is surrounded by a plurality of coaxially disposed and overlying outer tubular structures and where the length of the innermost tubular structure is greater than the length of each outer tubular structure and, moving from the innermost to the outermost outer tubular structure, the length of the outer tubular structures become progressively shorter.

21. The stent/graft as in claim 1 wherein the innermost tubular structure is surrounded by a plurality of coaxially disposed and overlying outer tubular structures and where the length of the innermost tubular structure is less than the length of each outer tubular structure and, moving from the innermost to the outermost tubular structure, the length of the outer tubular structures become progressively longer.

22. The stent/graft as in claim 1 wherein said structure configured to substantially preclude blood therethrough comprises about 72 to about 288 braided wires.

23. The stent/graft as in claim 1 wherein said structure configured to substantially preclude blood therethrough comprises braided wires having a diameter of about 0.001 to about 0.005 in.

24. The stent/graft as in claim 1 wherein said structure configured to substantially preclude blood therethrough exhibits fenestrations whose open areas are about 0.00015 to about 0.0003 square inches.

25. The stent/graft as in claim 1 wherein said structure configured to substantially preclude blood therethrough comprises fenestrations small enough to substantially preclude blood flow therethrough.

26. A preassembled catheter deliverable stent/graft for treating a vascular abnormality in a vessel wall, comprising:

an innermost tubular structure surrounded by at least one outer tubular structure, wherein said structures comprises braided wires of a highly elastic metal alloy, wherein at least one of said structures has a predetermined pick and pitch that defines fenestrations greater than about 0.001 square inches and, and wherein at least one of said structures has a predetermined pick and pitch that defines fenestrations smaller than about 0.002 square inches, and wherein the said structures have a similar pitch such that said structures are configured to be uniformly stretched to reduce radial dimensions thereof for facilitating insertion into a catheter and upon extraction from the catheter at the site of treatment, self-expand uniformly to engage the vessel wall.

\* \* \* \* \*